United States Patent
Terashima et al.

(12) 
(10) Patent No.: US 6,392,059 B1
(45) Date of Patent: May 21, 2002

(54) HYDRONAPHTHO[2,3-C]FURAN DERIVATIVES AND PROCESS FOR THE PREPARATION THEREOF

(75) Inventors: Shiro Terashima, Tokyo; Masanori Takadoi, Kuki; Akihiro Ishiwata, Tokyo; Tadashi Katoh, Machida, all of (JP)

(73) Assignees: Sagami Chemical Reasearch Center, Sagamihara; Kyorin Pharmaceutical Co., Ltd., Tokyo, both of (JP)

( * ) Notice: Subject to any disclaimer, the term of this patent is extended or adjusted under 35 U.S.C. 154(b) by 0 days.

(21) Appl. No.: 09/856,462

(22) PCT Filed: Dec. 10, 1999

(86) PCT No.: PCT/JP99/06937

§ 371 Date: Jun. 7, 2001

§ 102(e) Date: Jun. 7, 2001

(87) PCT Pub. No.: WO00/35898

PCT Pub. Date: Jun. 22, 2000

Related U.S. Application Data

(63) Continuation of application No. 08/367,771, filed on Jan. 3, 1906, now abandoned.

(30) Foreign Application Priority Data

Dec. 11, 1998 (JP) ............................................. 10-352991
Dec. 8, 1999 (JP) ........................................... 11-348326

(51) Int. Cl.⁷ .................... C07D 307/92; C07D 493/18; C07D 307/77; A61K 31/365
(52) U.S. Cl. ...................... 549/229; 549/298; 549/299; 549/458; 514/458; 514/473
(58) Field of Search ................................ 549/229, 298, 549/299, 458; 514/468, 473

(56) References Cited

U.S. PATENT DOCUMENTS 6,063,847 A * 5/2000 Chackalamanni et al. .. 524/297

FOREIGN PATENT DOCUMENTS

| WO | WO 93/18772 | 9/1993 |
| WO | WO 99 26943 A | 6/1999 |

OTHER PUBLICATIONS

Hart et al. Org. Chem. 1997, 62, 5023–5033.*
Baldwin et al. Tetrahedron letters.*
D. J. Hart, et al., Journal of Organic Chemistry, vol. 62, No 15, pp. 5023–5033, "Applications of Organnosulfur Chemistry to Organic Synhesis: Total Synthesis of (+) –Hymbeline and (+)–Himbacine", 1997.

J. E. Baldwin, et al., Tetrahedron Letters, vol. 36, No. 52, pp. 9551–9554, "Studies Towards a Postulated Biomimetic Diels–Alder Reaction for the Synthesis of Himgravine", 1995.

M. Takadoi, et al.: "A Novel Total Synthesis of (#)–Himbacine, A Potent Antagonist of the Muscarinic Recrptor of M2 Subtype", TETRAHEDRON LETTERS, vol. 40, No. 17, pp. 3399–3402, 1999.

D.Doller, et al.: "Design, synthesis, and structure–activity relationship studies of himbacine derived muscarinic receptor antagonists", BIOORGANIC & MEDICINAL CHEMISTRY LETTERS, vol. 9, No. 6, pp. 901–906, 1999.

S. Chackalamannil, et al.: "A highly efficient total synthesis of (#)–Himbacine", Journal of the American Chemical Society, vol. 118, No. 40, pp. 9812–9813, 1996.

* cited by examiner

*Primary Examiner*—Floyd D. Higel
*Assistant Examiner*—Kamal Saeed
(74) *Attorney, Agent, or Firm*—Oblon, Spivak, McClelland, Maier & Neustadt, P.C.

(57) ABSTRACT

Intermediates for the preparation of himbacine exhibiting muscarinic M2 receptor antagonism, which are hydronaphtho[2,3-c]furan derivatives represented by general formula (1) or intermediates for the preparation thereof:

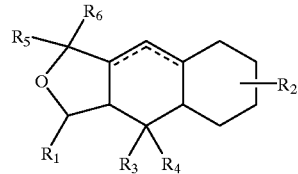

(1)

wherein $R_1$ is lower alkyl or aralky; $R_2$ is hydrogen, lower alkyl or aralkyl; $R_3$ and $R_4$ together represent oxygen or methylene, or alternatively $R_4$ is hydroxyl, lower alkoxy, aralkyloxy or lower acyloxy, with $R_3$ being hydrogen; $R_5$ and $R_6$ together represent oxygen, or alternatively $R_6$ is hydroxyl, lower alkxy, aralkyloxy or lower acyloxy, with $R_5$ being hydrogen; and either of the broken lines is a single bond and the other thereof is a double bond, or alternatively both are single bonds.

6 Claims, No Drawings

HYDRONAPHTHO[2,3-C]FURAN DERIVATIVES AND PROCESS FOR THE PREPARATION THEREOF

TECHNICAL FIELD

The present invention relates to novel hydronaphtho[2,3-c]furan derivatives being preparative intermediates of himbacine, which exhibits potent and selective antagonism against muscarinc $M_2$ receptor and is expected for the use as a therapeutic drug of Alzheimer's disease, and process for preparing the same.

BACKGROUND TECHNOLOGIES

Himbacine is a piperidine alkaloid, which was isolated from Galbulimima baccata being one species of pinaceous plant and the structure of which was determined in 1956, and, as the structural characteristics thereof, three points of condensation of 5-membered lactone ring to thermodynamically stable transdecalin ring in cis configuration, eight asymmetric centers including four internuclear hydrogens, and further binding of 3-cyclic portion with piperidine ring via trans double bond can be mentioned.

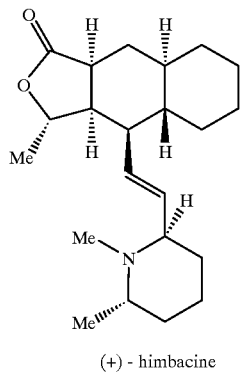

(+) - himbacine

In recent years, the senile dementia represented by Alzheimer type dementia has posed a significant problem socially and a substantial therapeutic drug therefore is desired earnestly. As one of approaches, from a phenomenon of decreased function of central cholinergic nerve in demential patients, development of therapeutic drugs based on so-called "choline hypothesis" is being advanced actively. Roughly classifying them, it is possible to divide into four below. Namely, they are (1) inhibitor of taking-in of choline, (2) inhibitor of acetylcholinesterase, (3) activator for synthesizing choline acetyltransferase and (4) compound acting on muscarine receptor (muscarine $M_1$ against or $M_2$ receptor antagonist). It has become clear recently that the himbacine exhibits potent and selective antagonistic action on $M_2$ receptor that is considered to suppress the release of nerve terminal acetylcholine, hence the potential as an antidemential drug has been found.

As described, the himbacine is a globally noteworthy compound from two points of potent activity and interesting chemical structure and, in recent years, its syntheses are reported by some groups. Thereamong, overall syntheses having intramolecular Diels-Alder reaction as a key reaction in all cases have been accomplished by groups of Kozikowski et al and Chackalamannil et al (Kozikowski, A. P. et al, J. Am. Chem. Soc., 1995, 117, 9369. Chackalamannil, S. et al, J. Am. Chem. Soc., 1996, 118, 9812). With these processes using intramolecular Diels-Alder reaction, however, there are problems of not only necessity for passing through troublesome processes in the synthesis of its skeleton, but also difficult synthesis of affinous compounds that become important for aiming at improved activity and decreased side effect. While, if using intermolecular Diels-Alder reaction, required constitutional units can be synthesized separately and each can be combined arbitrarily to react, thereby leading to easy synthesis of affinous compounds. However, its is the status quo that the synthesis of himbacine having such intermolecular Diels-Alder reaction as a key reaction has not yet been accomplished.

DISCLOSURE OF THE INVENTION

As a result of diligent studies in view of the subjects aforementioned, the inventors have found that the following inventive compounds are useful as the intermediates in the preparation of himbacine using the intermolecular Diels-Alder reaction as a key reaction, leading to the completion of the invention.

Namely, the invention provides hydronaphtho[2,3-c]furan derivatives represented by a following general formula (1)

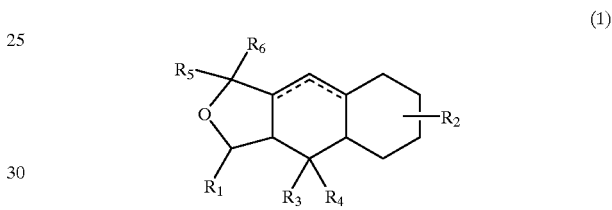

(1)

(wherein $R_1$ denotes a lower alkyl group or substituted or unsubstituted aralkyl group, $R_2$ denotes a hydrogen atom, lower alkyl group or substituted or unsubstituted aralkyl group, $R_3$ and $R_4$ unitedly denote an oxygen atom or methylene group, or $R_3$ denotes a hydrogen atom and $R_4$ denotes a hydroxyl group, lower alkoxy group, substituted or unsubstituted aralkyloxy group or lower acyloxy group, $R_5$ and $R_6$ unitedly denote an oxygen atom, or $R_5$ denotes a hydrogen atom and $R_6$ denotes a hydroxyl group, lower alkoxy group, substituted or unsubstituted aralkyloxy group or lower acyloxy group, and, in the case of broken lines accompanied, one denotes single bond and the other denotes double bond, or both denote single bonds), hydronaphtho [2,3-c]furan derivatives represented by a following general formula (1-1)

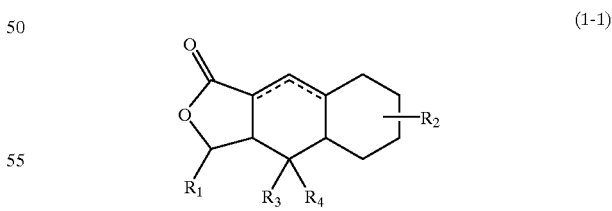

(1-1)

(wherein $R_1$ denotes a lower alkyl group or substituted or unsubstituted aralkyl group, $R_2$ denotes a hydrogen atom, lower alkyl group or substituted or unsubstituted aralkyl group, $R_3$ and $R_4$ unitedly denote an oxygen atom or methylene group, or $R_3$ denotes a hydrogen atom and $R_4$ denotes a hydroxyl group, lower alkoxy group, substituted or unsubstituted aralkyloxy group or lower acyloxy group, and in the case of broken lines accompanied, one denotes single bond and the other denotes double bond, or both denote single bonds), hydronaphtho[2,3-c]furan derivatives represented by a following general formula (1-2)

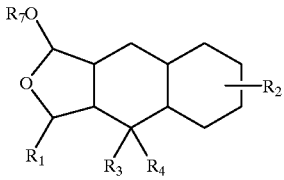
(1-2)

(wherein $R_1$ denotes a lower alkyl group or substituted or unsubstituted aralkyl group, $R_2$ denotes a hydrogen atom, lower alkyl group or substituted or unsubstituted aralkyl group, $R_3$ and $R_4$ unitedly denote an oxygen atom or methylene group, or $R_3$ denotes a hydrogen atom and $R_4$ denotes a hydroxyl group, lower alkoxy group, substituted or unsubstituted aralkyloxy group or lower acyloxy group, and $R_7$ denotes a hydrogen atom, lower alkyl group, substituted or unsubstituted daralkyl group or lower acyl group), hydronaphtho[2,3-c]furan derivatives represented by a following general formula (2)

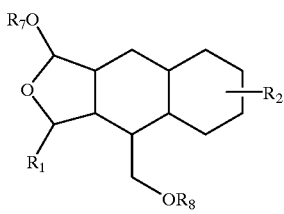
(2)

(wherein $R_1$ denotes a lower alkyl group or substituted or unsubstituted aralkyl group, $R_2$ denotes a hydrogen atom, lower alkyl group or substituted or unsubstituted aralkyl group, $R_7$ denotes a hydrogen atom, lower alkyl group, substituted or unsubstituted aralkyl group or lower acyl group), and $R_8$ denotes a hydrogen atom or protective group of hydroxyl group), and hydronaphtho[2,3-c]furan derivatives represented by a following general formula (3)

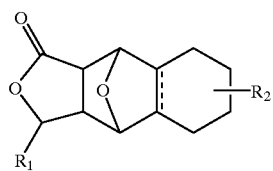
(3)

(wherein $R_1$ denotes a lower alkyl group or substituted or unsubstituted aralkyl group, $R_2$ denotes a hydrogen atom, lower alkyl group or substituted or unsubstituted aralkyl group, and, in the case of broken line accompanied, it denotes single bond or double bond), and a process for preparing compounds represented by a following general formula (3a)

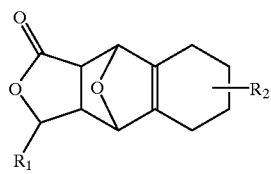
(3a)

(wherein $R_1$ denotes a lower alkyl group or substituted or unsubstituted aralkyl group, and $R_2$ denotes a hydrogen atom, lower alkyl group or substituted or unsubstituted aralkyl group), characterized by reacting compounds represented by a following general formula (4)

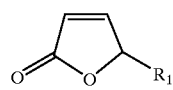
(4)

(wherein $R_1$ denotes a lower alkyl group or substituted or unsubstituted aralkyl group), with compounds represented by a following general formula (5)

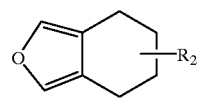
(5)

(wherein $R_2$ denotes a hydrogen atom, lower alkyl group or substituted or unsubstituted aralkyl group).

In the invention, for "lower alkyls", straight chain or branched ones with carbon atoms of 1 to 6 such as methyl, ethyl, 1-methylethyl, 1,1-dimethylethyl, propyl and 2-methylpropyl are mentioned and it doesn't matter whether saturated or unsaturated. For "aralkyl groups", benzyl group, 1-phenylethyl group, etc. are mentioned and, as substituents, lower alkyl group, lower alkoxy group, halogen atom, cyano group, nitro group, etc. are mentioned. For "lower alkoxy group", straight chain or branched ones with carbon atoms of 1 to 6 such as methoxy, ethoxy, 1-methylethoxy, 1,1-dimethylethoxy, propoxy and 2-methylpropoxy are mentioned and it doesn't matter whether saturated or unsaturated. For "aralkyloxy groups", benzyloxy group, 1-phenylethoxy group, etc. are mentioned and, as substituents, lower alkyl group, lower alkoxy group, halogen atom, cyano group, nitro group, etc. are mentioned. For "lower acyl groups", ones with carbon atoms of 1 to 6 such as formyl group, acetyl group, propionyl group and 2,2-dimethylpropionyl group are mentioned, and, for "lower acyloxy groups", ones with carbon atoms of 1 to 6 such as formyloxy group, acetoxy group, propionyloxy group and 2,2-dimethylpropionyl group are mentioned. Moreover, for the protective groups of hydroxyl group, trialkylsilyl groups such as trimethylsilyl group and t-butyldimethylsilyl group, arylmethyl groups such as benzyl group and diphenylmethyl group, acyl groups such as acetyl group and propionyl group, lower alkoxymethyl groups such as methoxymethyl group and ethoxymethyl group, aralkyloxymethyl groups such as benzyloxymethyl group, tetrahydropyranyl group, and the like are mentioned, and the introduction and elimination thereof can be performed by appropriately adopting the methods described in the literature (Green, T. W.; Wuts, P. G. M. "Protective Groups in Organic Synthesis", $2^{nd}$ Ed., Wiley Interscience Publication, John-Weiley & Sons, New York, 1991, pp 14–118).

The compounds of said general formula (4) can be prepared by publicly known processes (Beckmann, M. et al, Tetrahedron: Asymmetry, 1990, 1, 335 etc.). Similarly, the compounds of general formula (5) can be prepared by publicly known processes (Spencer, T. A. et al, J. Am. Chem. Soc., 1973, 95, 250 etc.). Besides the inventive compounds have a plurality of asymmetric carbon atoms and corresponding optical isomers can exist, but these optical isomers and their mixtures are to be included in the invention.

The compounds represented by general formula (1) and (2) in the invention can be prepared according to following preparative processes, making the compounds represented by said general formula (3a) synthesizable from the compounds represented by said general formula (4) and (5) as key intermediates.

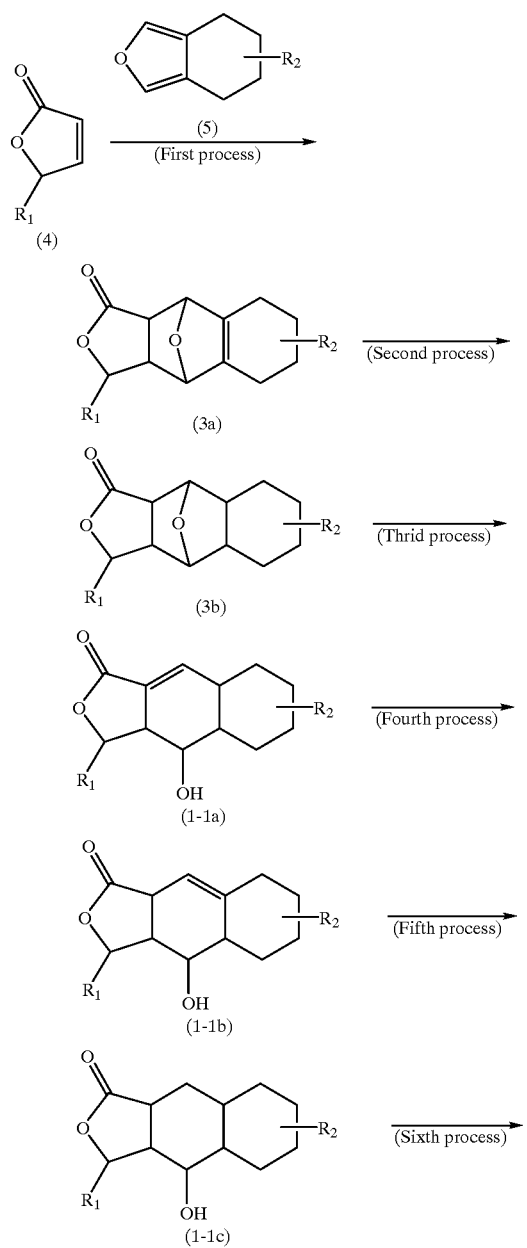

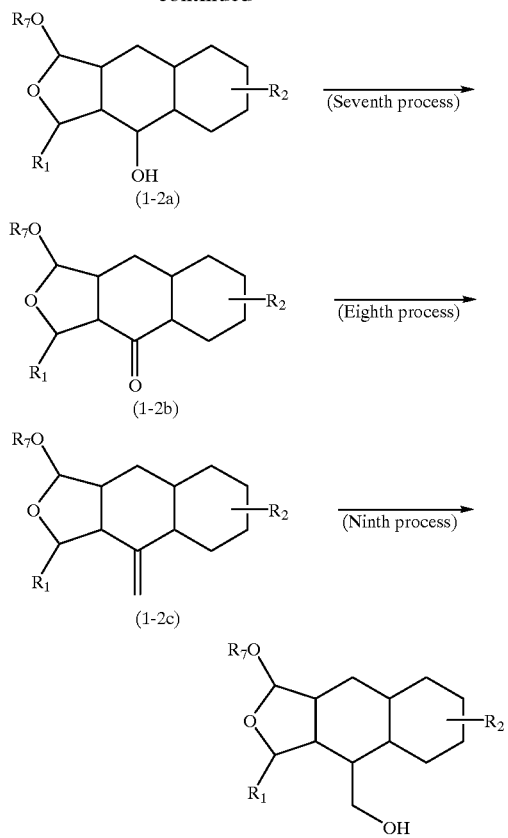

(First process)

This process is for preparing 4,9-epoxyoctahydronaphtho [2,3-c]furan-1(3H)-one derivatives represented by said general formula (3a) by adding 4,5,6,7-tetrahydroisobenzofuran represented by said general formula (5) to (S)-5-lower alkyl-2(5H)-furanone represented by said general formula (4).

This reaction can be conducted in the presence or absence of Lewis acid such as zinc chloride, zinc bromide, zinc iodide, boron trifluoride, aluminum chloride, tin tetrachloride, boron trifluoride-diethyl ether complex or lithium perchlorate, rhodium complex such as Wilkinson's complex, sodium dodecylsulfate or cetyltrimethyl ammonium bromide. The reaction is conducted in the presence or absence of, for example, hydrocarbonic solvent such as pentane, hexane, cyclohexane, benzene, toluene or xylene, halogenated hydrocarbonic solvent such as dichloromethane, 1,2-dichloroethane, chloroform or carbon tetrachloride, ethereal solvent such as diethyl ether, tetrahydrofuran or 1,4-dioxane, aprotic polar solvent such as acetonitrile, propionitrile, nitromethane, nitroethane, N,N-dimethylformamide or dimethyl sulfoxide, or mixed solvent of one of these with water, and usually proceeds smoothly at −20° C. to 200° C. Also, as the case may be, stabilizers like radical eliminator such as 2,6-di-t-butyl-4-methylphenol (BHT), etc. may be added.

(Second process)

This process is for catalytically reducing the double bond in 4,9-epoxyoctahydronaphtho[2,3-c]furan-1(3H)-one derivatives represented by said general formula (3a), obtainable in the first process aforementioned, to prepare 4,9-epoxyoctahydronaphtho[2,3-c]furan-1(3H)-one derivatives represented by said general formula (3b).

This reaction is conducted usually in solvent, using catalyst such as palladium-carbon, Raney nickel, palladium hydroxide, rhodium-alumina or platinum oxide. As a solvent, any can be used, if it doesn't take part in the reaction, but, for example, hydrocarbonic solvent such as pentane, hexane, cyclohexane, benzene, toluene, or xylene, halogenated hydrocarbonic solvent such as dichloromethane, 1,2-dichloroethane, chloroform or carbon tetrachloride, ethereal solvent such as diethyl ether, tetrahydrofuran or 1,3-dioxane, alcoholic solvent such as methanol, ethanol, 1-propanol, 2-propanol, 1-butanol, 2-butanol, 2-methyl-1-propanol or 2-methyl-2-propanol, or mixed solvent of one of these with water is used preferably. The reaction proceeds smoothly at 0° C. to 100° C. under 101.3 KPa to several hundreds KPa.

(Third process)

This process is for cutting the ether bond of 4,9-epoxydecahydronaphtho[2,3-c]furan-1(3H)-one derivatives represented by said general formula (3b), obtainable in the second process aforementioned, to prepare octahydronaphtho[2,3-c]furan-1(3H)-one derivatives represented by said general formula (1-1a).

This reaction can be conducted usually in the presence of suitable reactant, for example, alkali metal alkoxide such as sodium methoxide or sodium ethoxide, alkali metal organic base such as n-butyl lithium, lithium bis(trimethylsilyl) amide, sodium bis(trimethylsilyl)amide or potassium bis (trimethylsilyl)amide, tertiary organic base such as triethylamine, diisopropylethylamine, pyridine, N-methylmorpholine, imidazole, pyrrolidine, piperidine, 1,5-diazabicyclo[4.3.0]nona-5-ene or 1,8-diazabicyclo [5.4.0]ude-7-cene, or Lewis acid such as zinc chloride, zinc bromide, zinc iodide, boron trifluoride, aluminum chloride, tin tetrachloride, boron trifluoride-diethyl ether complex or lithium perchlorate. As a solvent, any can be used, if it doesn't take part in the reaction, but, for example, hydrocarbonic solvent such as pentane, hexane, cyclohexane, benzene, toluene or xylene, halogenated hydrocarbonic solvent such as dichloromethane, 1,2-dichloroethane, chloroform or carbon tetrachloride, or ethereal solvent such as diethyl ether, tetrahydofuran or 1,4-dioxane is used preferably. The reaction proceeds smoothly at −110° C. to 100° C.

(Fourth process)

This process is for isomerizing the double bond of octahydronaphtho[2,3-c]furan-1(3H)-one derivatives represented by said general formula (1-1a), obtainable in the third process aforementioned, using a suitable base, to prepare octahydronaphto-[2,3-c]furan-1(3H)-one derivatives represented by said general formula (1-1b).

This reaction can be conducted in the presence of, for example, alkali metal alkoxide such as sodium methoxide or sodium ethoxide, alkali metal organic base such as n-butyl lithium, lithium bis(trimethylsilyl)amide, sodium bis (trimethylsilyl)amide or potassium bis(trimethylsilyl)amide, or tertiary organic base such as triethylamine, diisopropylethylamine, pyridine, N-methyl-morpholine, imidazole, pyrrolidine, piperidine, 1,5-diazabicyclo-[4.3.0] nona-5-ene or 1,8-diazabicyclo[5.4.0]unde-7-cene. As a solvent, any can be used, if it doesn't take part in the reaction, but, for example, hydrocarbonic solvent such as pentane, hexane, cyclohexane, benzene, toluene or xylene, halogenated hydrocarbonic solvent such as dichloromethane, 1,2-dichloroethane, chloroform or carbon tetrachloride, ethereal solvent such as diethyl ether, tetrahydrofuran or 1,4-dioxane, or alcoholic solvent such as methanol, ethanol, 1-propanol, 2-propanol, 1-butanol, 2-butanol, 2-methyl-1-propanol or 2-methyl-2-propanol is used preferably. The reaction proceeds smoothly at −110° C. to 100° C.

(Fifth process)

This process is for catalytically reducing the double bond in octahydronaphtho[2,3-c]furan-1(3H)-one derivatives represented by said general formula (1-1b), obtainable in the fourth process aforementioned, to prepare decahydronaphtho[2,3-c]furan-1(3H)-one derivatives represented by said general formula (1-1c).

This reaction is conducted usually in solvent, using catalyst such as palladium-carbon, Raney nickel, palladium hydroxide, rhodium-alumina or platinum oxide. As a solvent, any can be used, if it doesn't take part in the reaction, but, for example, hydrocarbonic solvent such as pentane, hexane, cyclohexane, benzene, toluene or xylene, halogenated hydrocarbonic solvent such as dichloromethane, 1,2-dichloroethane, chloroform or carbon tetrachloride, ethereal solvent such as diethyl ether, tetrahydrofuran or 1,4-dioxane, alcoholic solvent such as methanol, ethanol, 1-propanol, 2-propanol, 1-butanol, 2-butanol, 2-methyl-1-propanol or 2-methyl-2-propanol, or mixed solvent of one of these with water is used preferably. The reaction proceeds smoothly at 0° C. to 100° C. under 98.1 KPa to several hundreds KPa. Besides, when using platinum oxide for catalyst, only single isomer can be obtained selectively.

(Sixth process)

This process is for reducing the lactonecarbonyl bond in decahydronaphtho[2,3-c]furan-1(3H)-one derivatives represented by said general formula (1-1c), obtainable in the fifth process aforementioned, and further for protecting 1-hydroxyl group of 1,4-dihydroxy-dodecahydronaphtho[2, 3-c]furan derivatives produced by selective alkylation, to prepare 1-alkoxy-4-hydroxy-dodecahydronaphtho[2,3-c] furan derivatives represented by said general formula (1-2a).

The reduction of this reaction is conducted by using dialkylaluminum hydride such as diisobutylaluminum hydride. As a solvent, any can be used, if it doesn't take part in the reaction, but, for example, hydrocarbonic solvent such as pentane, hexane, cyclohexane, benzene, toluene or xylene, halogenated hydrocarbonic solvent such as dichloromethane, 1,2-dichloroethane, chloroform or carbon tetrachloride, or ethereal solvent such as diethyl ether, tetrahydrofuran or 1,4-dioxane is used. The reaction proceeds smoothly at −100° C. to 100° C. The etherification of 1-position hydroxyl group to be conducted successively is performed in alcohol solvent in the presence of a suitable Lewis acid. As the "suitable Lewis acid", for example, zinc chloride, zinc bromide, zinc iodide, boron trifluoride, aluminum chloride, tin tetrachloride, boron trifluoride-diethyl ether complex, lithium perchlorate or the like is mentioned, and, as the alcohol solvent, for example, alcoholic solvent such as methanol, ethanol, 1-propanol, 2-propanol, 1-butanol, 2-butanol, 2-methyl-1-propanol or 2-methyl-2-propanol is used preferably. The reaction usually proceeds smoothly at −100° C. to 100° C.

Moreover, the introduction of aralkyl group or acyl group to 1-position hydroxyl group to be conducted successively is performed according to publicly known methods (Green, T. W.; Wuts, P. G. M. "Protective Groups in Organic Synthesis", $2^{nd}$ Ed., Wiley Interscience Publication, John-Weiley & Sons, New York, 1991, pp 46–66 and pp 87–118).

(Seventh process)

This process is for oxidizing the 4-position hydroxyl group in 4-hydroxydodecahydronaphtho[2,3-c]furan derivatives represented by said general formula (1-2a), obtainable in the sixth process aforementioned, to prepare 4-oxo-dodecahydronaphtho[2,3-c]furan derivatives represented by said general formula (1-2b).

As the oxidizing agent to be used in this process, chromic acid, chromic trioxide-pyridine mixed system, dimethyl sulfoxide-oxalyl chloride-triethylamine mixed system, ruthenium complex, Dess-Martin reagent or the like can be used. The oxidation is usually preferable to be conducted in solvent and, for example, halogenated hydrocarbonic solvent such as dichloromethane, 1,2-dichloroethane, chloroform or carbon tetrachloride is used. The reaction proceeds smoothly at −100° C. to 100° C.

(Eighth process)

This reaction is for conducing Wittig reaction by reacting ylide prepared from methyltriphenylphosphonium salt and base, with 4-position carbonyl group in 4-oxo-dodecahydronaphtho[2,3-c]furan derivatives represented by said general formula (1-2b), obtainable in the seventh process aforementioned, to prepare 4-methylenedodecahydronaphtho[2,3-c]furan derivatives represented by said general formula (1-2c).

As the phosphonium salt to be used in this process, for example, methyltriphenylphosphonium chloride, methyltriphenylphosphonium bromide or methyltriphenylphosphonium iodide is mentioned, and the reaction can be conducted in the presence of, for example, alkali metal alkoxide such as sodium methoxide or sodium ethoxide, alkali metal organic base such as n-butyl lithium, lithium bis(trimethylsilyl)amide, sodium bis(trimethylsilyl)amide or potassium bis(trimethylsilyl)amide, or tertiary organic base such as triethylamine, diisopropylethylamine, pyridine, N-methylmorpholine, imidazole, pyrrolidine, piperidine, 1,5-diazabicyclo[4.3.0]non-5-ene or 1,8-diazabicyclo[5.4.0]undec-7-ene as a base to be used. As a solvent, any can be used, if it doesn't take part in the reaction, but, for example, hydrocarbonic solvent such as pentane, hexane, cyclohexane, benzene, toluene or xylene, halogenated hydrocarbonic solvent such as dichloromethane, 1,2-dichloroethane, chloroform or carbon tetrachloride, ethereal solvent such as diethyl ether, tetrahydrofuran or 1,4-dioxane, or alcoholic solvent such as methanol, ethanol, 1-propanol, 2-propanol, 1-butanol, 2-butanol, 2-methyl-1-propanol or 2-methyl-2-propanol is used preferably. The reaction proceeds smoothly at −110° C. to 100° C.

(Ninth process)

This reaction is for conducting hydroboraton and oxidation reaction to 4-position methylene group in 4-methylenedodecahydronaphtho[2,3-c]furan derivatives represented by said general formula (1-2c), obtainable in the eighth process aforementioned, to prepare 4-hydroxymethyl-dodecahydronaphtho[2,3-c]furan derivatives represented by said general formula (2a).

As a hydroborating agent to be used in this reaction, for example, borane-tetrahydrofuran complex, borane-dimethyl sulfide complex, 9-borabicyclo[3,3,1]nonane or the like is mentioned and, as a solvent, any can be used, if it doesn't take part in the reaction, but, for example, hydrocarbonic solvent such as pentane, hexane, cyclohexane, benzene, toluene or xylene, halogenated hydrocarbonic solvent such as dichloromethane, 1,2-dichloroethane, chloroform or carbon tetrachloride, ethereal solvent such as diethyl ether, tetrahydrofuran or 1,4-dioxane, or mixed solvent thereof is used. The reaction proceeds smoothly at −110° C. to 200° C. In the oxidation reaction to be conducted next, aqueous hydrogen peroxide, m-chloroperbenzoic acid, peracetic acid or the like is used. As a solvent, any can be used, if it doesn't take part in the reaction, but, for example, hydrocarbonic solvent such as pentane, hexane, cyclohexane, benzene, toluene or xylene, halogenated hydrocarbonic solvent such as dichloromethane, 1,2-dichloroethane, chloroform or carbon tetrachloride, ethereal solvent such as diethyl ether, tetrahydrofuran or 1,4-dioxane, alcoholic solvent such as methanol, ethanol, 1-propanol, 2-propanol, 1-butanol, 2-butanol, 2-methyl-1-propanol or 2-methyl-2-propanol, or mixed solvent of one of these with water is used preferably. The reaction proceeds smoothly at −110° C. to 100° C.

The 4-hydroxy-dodecahydronaphtho[2,3-c]furan derivatives represented by said general formula (2a), synthesized through the synthetic processes as described above are derived to 4-phenylsulfonylmethyl-decahydronaphtho[2,3-c]furan derivatives by sulfonation of 4-position hydroxymethyl group, substitution of 4-position sulfonyloxymethyl group with phenylthio group, and oxidation of 4-position phenylthiomethyl group to phenylsulfonylmethyl group, according to the synthetic method of Kozikowski et al (Kozikowski, A. P. et al, J. Am. Chem. Soc., 1995, 117, 9369) (see Referential example 1).

Furthermore, the inventors confirmed that, by using 4-phenylsulfonylmethyl-decahydronaphtho[2,3-c]furan derivatives obtained as optically active substances and converting these according to the method described in literature (Kozikowski, A. P. et al, J. Am. Chem. Soc., 1995, 117, 9369), natural type himbacine could be synthesized (see Referential examples 2 through 4).

In following, the invention will be illustrated in detail bases on examples and Referential examples, but it goes without saying that the invention is not confined to these.

Best embodiment to put the invention into practice

EXAMPLE 1

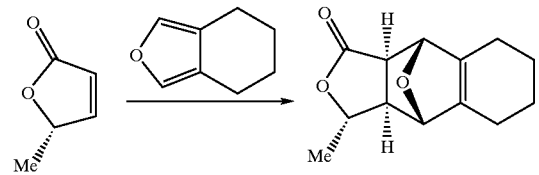

To 224.0 mg(2.28 mmol) of (S)-5-methyl-2(5H)-furanone were added 557.9 mg(1.5 equivalents) of 4,5,6,7-tetrahydroisobenzofuran in 2 ml of dehydrated ether solution and 1.06 g of lithium perchlorate, and, after flushing with argon, the mixture was stirred for 168 hours at room temperature. The reaction mixture was poured into 20 ml of water, which was extracted with methylene chloride(10 ml×3). The organic layer was dried over anhydrous magnesium sulfate, filtered and solvent was distilled off under reduced pressure. The residue was purified by means of silica gel column chromatography(methylene chloride, then methylene chloride:ethyl acetete=10:1) to obtain 292.2 mg of (3S, 3aS, 4S, 9R, 9aR)-4,9-epoxy-3-methyl-3a,4,5,6,7,8,9,9a-octahydronaphtho[2,3-c]furan-1(3H)-one (yield 58%).

mp. 141–144° C. Colorless powdery crystals; $^1$H NMR (400 MHz, CDCl$_3$): 1.45(3H,d,J=6.4) 1.48–1.55(2H,m) 1.63–1.71(2H,m) 1.84–1.96(2H,m 2.18–2.30(2H,m) 2.28 (1H,dd,J=7.6,3.2) 2.87(1H,d,J=7.8) 4.48(1H,qd,J=6.4,3.4) 4.72(1H,brs) 5.03(1H,brs); IR(KBr): 1750 cm$^{-1}$; HRCIMS: Calcd. for C$_{13}$H$_{17}$O$_3$: 21.1178 Found: 221.1176.

EXAMPLE 2

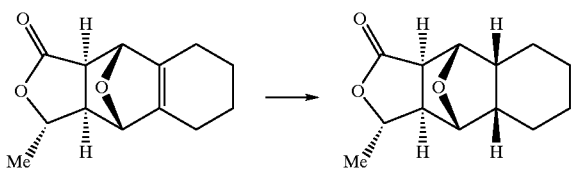

To 79.4 mg(0.36 mmol) of (3S, 3aS, 4S, 8R, 9aR)-4,9-epoxy-3-methyl-3a,4,5,6,7,8,9,9a-octahydronaphtho[2,3-c]furan-1(3H)-one in 5 ml of ethanol solution were added 8.00 mg (10% by weight) of 10% palladium-carbon, and catalytic reduction was conducted at ambient temperature under 98.1 Kpa. After stirring for 12 hours, the reaction mixture was filtered through celite and the residue was washed using 20 ml of ethyl acetate. Combined organic layers were distilled off under reduced pressure to obtain 76.7 mg of (3S,3aS,4R,4aS,8aR,9S,9aR)-4,9-epoxy-3-methyl-decahydronaphtho[2,3-c]furan-1(3H)-one (yield 96%).

$[\alpha]_D^{20}$+38° (c 0.51, CHCl$_3$); mp. 158–159° C. (hexane-ethyl acetate) Colorless needle-like crystals; $^1$H NMR(400 MHz, CCCl$_3$): δ 1.02–1.18(2H,m) 1.32–1.56(4H,m) 1.40 (3H,d,J=6.4) 1.69–1.75(2H,m 2.00–2.15 1.40(3H,d,J=6.4) 1.69–1.75(2H,m 2.00–2.15(2H,m) 2.50(1H,dd,J=8.3,3.4) 3.12(1H,d,J=7.8) 4.39)1H,qd,J=6.4,3.4) 4.40(1H,dJ=3.9) 4.75(1H,d,J=4.9); $^{13}$C NMR(125 MHz, CDCl$_3$): δ 19.5, 19.5, 19.6, 19.9, 22.5, 38.9, 39.7, 45.9, 46.3, 81.2, 83.7, 85.6, 178.0 IR(KBr): 1750 cm$^{-1}$; HRCIMS: Calcd. for C$_{13}$H$_{19}$O$_3$: 223.1334 Found: 223.1338; Elemental analysis: Calcd. for C$_{13}$H$_{18}$O$_3$; C: 70.24; H: 8.16; Found: C: 69.97; H: 8.40

EXAMPLE 3

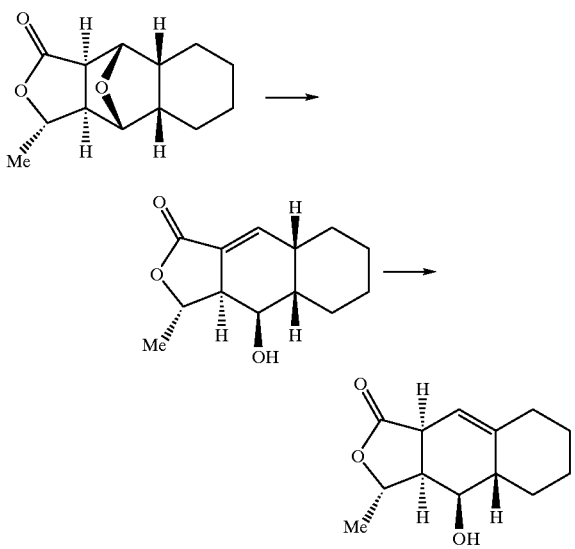

To 110.0 mg(0.50 mmol of (3S,3aS,4R,4aS,8aR,9S, 9aR)-4,9-epoxy-3-methyl-decahydronaphtho[2,3-c]furan-1(3H)-one in 20 ml of dehydrated tetrahydrofuran solution were added dropwise 2.50 ml(5 equivalents) of lithium bis(trimethylsilyl)amide-tetrahydrofuran solution (1M) at −78° C. (internal temperature) under an atmosphere of argon, and the mixture was stirred for about 4 hours while raising temperature naturally. At −40° C., 2 ml of saturated aqueous solution of ammonium chloride were added, which was stirred at room temperature, and solvent was distilled off under reduced pressure. To the residue was added 10 ml of water, which was extracted with ether(5 ml×3). The organic layer was dried over anhydrous magnesium sulfate, filtered and solvent was distilled off. The residue was purified by means of silica gel column chromatography(hexane:ethyl acetate=2:1) to obtain 100.9 mg of (3S,3aS,4R,4aS,8aR)-4-hydroxy-3-methyl-3a,4,4a,5,6,7,8,8a-octahydronaphtho[2,3-c]furan-1(3H)-one (yield 92%).

mp. 191–193° C. (hexane-ethyl acetate) Colorless powdery crystals; $^1$H NMR(400 MHz, CDCl$_3$): δ 0.94–1.29(4H, m) 1.41(1H,d,J=5.4) 1.52)3H,d,J=6.4) 1.56–1.77)(3H,m) 1.94–2.04(2H,m) 2.58–2.64(1H,m) 2.74–2.81(1H,m) 4.01–4.04(1H,m) 4.61(1H,dq,J=9.1,5.9) 6.69(1H,t,J=2.5); IR(KBr): 1730 cm$^{-1}$; HRCIMS: Calcd. for C$_{13}$H$_{18}$O$_3$; 223.1334 Found; 223.1303; Elemental analysis: Calcd. for C$_{13}$HR$_{18}$O$_3$; C: 70.24; H: 8.16; Found; C: 70.02; H: 8.13. Since this compound is unstable at room temperature, next reaction was conducted immediately. To 61.8 mg(0.28 mmol) of (3S,3aS,4R,4aS,8aR)-4-hydroxy-3-methyl-3a,4,-4a,5,6,7,8,8a-octahydronaphtho[2,3-c]furan-1(3H)-one in 2 ml of dehydrated toluene solution were added 207.9 μl (5 equivalents) of 1.8-diazabicyclo[5.4.0]undec-7-ene, and the mixture was stirred for 5 hours at about 100° C. After cooling, solvent was distilled off under reduced pressure and 10 ml of cold dilute hydrochloric acid were added, which was extracted with methylene chloride(5 ml×3). The organic layer was dried over anhydrous magnesium sulfate, filtered and solvent was distilled off. The residue was purified by means of silica gel column chromatography(hexane:ethyl acetate=1:1) to obtain 51.2 mg of (3S,3aS,4R,4aS,9aS)-4-hydroxy-3-methyl-3a,4,4a,5,6,7,8,9a-octahydronaphtho[2,3-c]furan-1(3H)-one (yield 83%).

$[\alpha]_D^{20}$+148° C. (c 0.29, CHCl$_3$); mp. 166–167 (hexane-ethyl acetate) Colorless platy crystals; $^1$H NMR(500 MHz, CDCl$_3$): δ 1.00(1H,qd,J=12.7,3.5) 1.17–1.32(1H,m) 1.36–1.48(1H,m) 1.52(3H,d,J=6.2) 1.69(1H,d,J=4.2 1.77–1.90(2H,m) 1.95–2.08(2H,m 2.17–2.25(1H,m) 2.33 (1H,dt,J=14.2,1.9) 2.56(1H,ddd,J=8.4,8.4,4.7) 3.29(1H,dq, J=8.6,3.0) 3.82(1H,dq,J=4.4,4.4) 4.60(1H,dq,J=8.6,6.2) 5.31(1H,d,J=2.4); $^{13}$C NMR(125 MHz, CDC$_{13}$): δ 21.9, 25.6, 26.9, 31.8, 34.6, 41.0, 43.9, 46.8, 72.4, 77.5, 112.8, 141.1, 176.0; IR(KBr): 1730 cm$^{-1}$; Elemental analysis: Calcd. for C$_{13}$H$_{18}$O$_3$; C: 70.24; H: 8.16; Found; C: 70.29; H: 8.31.

EXAMPLE 4

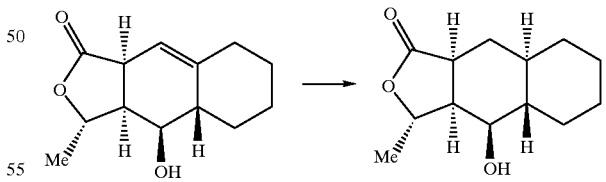

To 375.1 mg(1.69 mmol) of (3S,3aS,4R,4aS,9aS)-4-hydroxy-3-methyl-3a,4,4a,5,6,7,8,9a-octahydronaphtho[2,3-c]furan-1(3H)-one in 5 ml of ethanol solution were added 40.0 mg(10% by weight) of platinum oxide, and catalytic reduction was conducted at ambient temperature under 98.1 Kpa. After stirring for 16 hours, the reaction mixture was filtered through celite and the residue was washed using 20 ml of ethyl acetate. Combined organic layers were distilled off under reduced pressure and the residue was purified by means of silica gel column chromtography(methylene chloride:ethyl acetate=4:1) to obtain 363.7 mg of (3S,3aS,4R, 4aS,8aR,9aS)-4-hydroxy-3-methyl-decahydronaphtho[2,3-c]furan-1(3H)-one (yield 96%).

$[\alpha]_D^{20}$+28° (c 0.23, CHCl$_3$); mp. 195–196° C. (hexane-ethyl acetate) Colorless flaky crystals; $^1$H NMR(500 MHZ, CDCl$_3$): 0.81–0.92 (1H,m) 0.98–1.30(6H,m) 1.54(3H,d,J= 6.0) 1.69–1.77(2H,m) 1.74(1H,d,J=4.0) 1.80–1.87(2H,m) 2.04–2.10(1H,m) 2.51(1H,ddd,J=6.7,10.1,6.7) 2.67(1H,dt, J=12.3,6.6) 3.65 (1H,ddd,J=10.2,6.1,4.0) 4.73(1H,dq,J= 11.9,6.0); $^{13}$C NMR(125 MHZ, CDCl$_3$): δ (22.1, 25.7, 25.7, 28.9, 31.7, 33.0, 38.6, 41.9, 44.3, 48.2, 73.4, 77.4, 177.8; IR(KBr): 3460, 1740 cm$^{-1}$; Elemental analysis: Calcd. for C$_{13}$H$_{20}$O$_3$; C: 69.61; H: 8.99; Found; C: 69.72; H: 8.93.

EXAMPLE 5

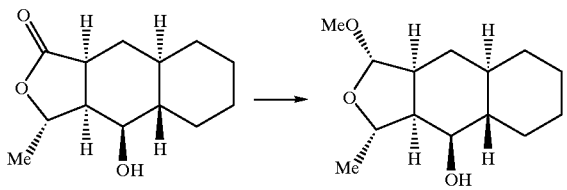

To 1.88 g(8.38 mmol) of (3S,3aS,4R,4aS,8aR,9aS)-4-hydroxy-3-methyl-decahydronaphtho[2,3-c]furan-1(3H)-one in 200 ml of dehydrated ether solution were added dropwise 26.7 ml(3 equivalents) of diisobutylalumium hydride-hexane solution(0.94 M) at −78° C. under an atmosphere of argon. After stirring for about 1 hour at the same temperature, methanol-water mixed solution (10 ml+10 ml) was added dropwise slowly and the mixture was stirred for 1 hour at room temperature. Solvent was distilled off and 100 ml of ethyl acetate were added to the residue, which was filtered through celite, and the residue was washed with ethyl acetate(50 ml). Solvent was distilled off and 100 ml of saturated brine were added, which was extracted with methylene chloride(30 ml×3). The organic layer was dried over anhydrous magnesium sulfate, filtered and solvent was distilled off to obtain crude lactol form. This was dissolved into a mixed solution of 50 ml of dehydrated methanol with 50 ml of dehydrated methylene chloride, 1.55 ml(1.5 equivalents) of boron trifluoride-diethyl ether complex were added dropwise at −60° C. under an atmosphere of argon, and the mixture was stirred for about 12 hours while raising temperature naturally. To the reaction mixture were added 1.75 ml (1.5 equivalents) of triethylamine and, after stirring at room temperature, solvent was distilled of. To the residue was added 100 ml of cold dilute aqueous solution of sodium hydrogencarbonate, which was extracted with methylene chloride(30 ml×3). The organic layer was dried over anhydrous magnesium sulfate, filtered and solvent was distilled off. The residue was purified by means of silica gel column chromatography(hexane:ethyl acetate=2:1) to obtain 1.50 g of (1S,3S,3aS,4R,4aS,8aR,9aS)-4-hydroxy-1-methoxy-3-methyl-dodecahydronaphtho[2,3-c]furan (yield after two processes 74%).

$[\alpha]_D^{20}$+90° (c 0.21, CHCl$_3$); mp. 123–124° C. (hexane) Colorless needle-like crystals $^1$H NMR(500 MHz, CDCl$_3$): δ 0.81–1.04(4h,M) 1.13–1.30(3H,m) 1.39(3H,d,J=6.0) 1.45–1.53(2H,m) 1.60–21.74(2H,m) 1.77–1.84(1H,m) 2.04–2.11(1H,m) 2.20(1H,dt,J=12.3,6.0) 2.47(1H,dt,J=9.1, 6.0) 3.32(3H,s) 3.64(1H,ddd,J=9.6, 5.7,3.5) 4.30(1H,dq,J= 9.1,6.0) 4.53(1H,s); $^{13}$C NMR(125 MHz, CDCl$_3$): δ 25.0, 26.0, 26.0, 29.1, 32.7, 33.4, 38.6, 44.1, 46.0, 48.6, 54.0, 74.6, 76.4, 108.5; IR(KBr): 3407, 2976, 1447, 1437, 1364 cm$^{-1}$; Elemental analysis: Calcd. for C$_{14}$H$_{24}$O$_3$; C: 69.96, H: 10.07; Found; C: 69.72; H: 9.82

EXAMPLE 6

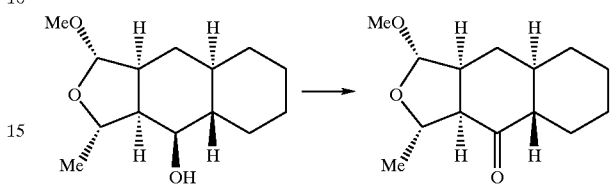

To 1.23 g(5.12 mmol) of (1S,3S,3aS,4R,4aS,8aR,9aS)-4-hydroxy-1-methoxy-3-methyl-dodecahydronaphtho[2,3-c]furan and 3.26 g of sodium hydrogencarbonate in 100 ml of methylene chloride suspension were added 3.26 g(1.5 equivalents) of Dess-Martin reagent under stirring and cooling with ice, and the mixture was stirred for 1 hour at room temperature. After 6.35 g of sodium thiosulfate 5-hydrate and 50 ml of saturated aqueous solution of sodium hydrogencarbonate were added to the reaction mixture and stirred, two layers were separated and extraction with methylene chloride(5 ml×3) was performed from aqueous layer. The organic layers were dried over anhydrous magnesium sulfate, filtered and solvent was distilled off. The residue was purified by means of silica gel column chromatography (hexane:ethyl acetate=4:1) to obtain 1.18 g of (1S,3S,3aR, 4aS,8aR,9aS)-1-methoxy-3-methyl-4-oxo-dodecahydronaphtho[2,3-c]furan (yield 97%).

Also, the synthesis was possible separately through following process. Namely, 0.77 g(1.50 equivalents) of N-methylmorpholine and 2.50 g of molecular sieve 4A(MS4A) were added to 1.05 g(4.37 mmol) of (1S,3S,3aS, 4R,4aS,8aR,9aS)-4-hydroxy-1-methoxy-3-methyl-dodecahydronaphtho[2,3-c]furan in 10 ml of methylene chloride solution, then 76.8 mg(0.05 equivalents) of tetra-propylammonium perruthenate(TPAP) were added, and the mixture was stirred for 1.5 hours at room temperature. The reaction mixture was filtered through celite and the residue was washed with ether(100 ml). The filtrate was washed with 10% aqueous solution of Na$_2$S$_2$O$_3$ and then with brine (each 20 ml×1). The organic layer was dried over anhydrous magnesium sulfate, filtered and solvent was distilled off to obtain 0.99 g of (1S,3S,3aR,4aS,8aR,9aS)-1-methoxy-3-methyl-4-oxo-dodecahydronaphtho[2,3-c]furan (yield 95%).

$[\alpha]_D^{20}$+165° (c 0.16, CHCl$_3$); mp. 86–87° C. (hexane) Colorless platy crystals; $^1$H NMR(500 MHz, CDCl$_3$): δ 1.10–1.50(6H,m) 1.33(3H,d,J=6.1) 1.68–1.86(4H,m) 1.96–2.03(2H,m) 2.59(1H,dt,J=12.7,6.3) 2.80(1H,dd,J=9.1, 6.9) 3.32(3H,s) 4.33(1H,dq,J=9.2,6.1) 4.71(1H,s); $^{13}$C NMR (125 MHz, CDCl3): δ 22.8, 25.1, 25.5, 25.6, 32.5, 34.3, 41.3, 49.5, 51.4, 54.1, 58.1, 78.4, 109.1, 210.8; IR(KBr): 2926, 1696, 1450 cm$^{-1}$; Elemental analysis: Calcd. for C$_{14}$H$_{22}O_3$; C: 70.56; H: 9.30; Found; C: 70.26; H: 9.29.

EXAMPLE 7

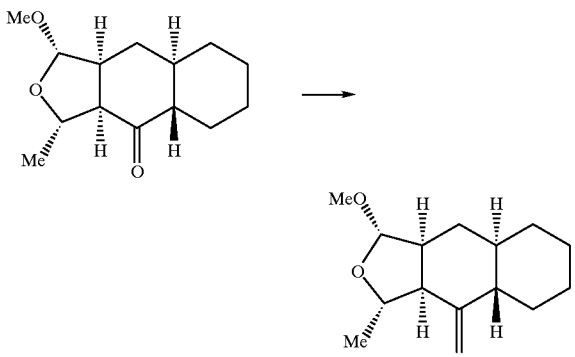

To 9.96 g(5 equivalents) of methyltriphenylphosphonium iodide in 400 ml of dehydrated ether suspension were added dropwise 4.1 ml(5 equivalents) of sodium bis(trimethylsilyl) amide-toluene solution(0.60M) under cooling with ice and under an atmosphere of argon. After stirring for 1 hour at room temperature, 1.17 g of (1S,3S,3aR,4aS,8aR,9aS)-1-methoxy-3-methyl-4-oxo-dodecahydronaphtho[2,3-c]furan (4.93 mmol) in 30 ml of dehydrated ether solution were added dropwise again under cooling with ice. After stirring for 2 hours at room temperature, 50 ml of cold saturated aqueous solution of ammonium chloride were added to the reaction mixture and solvent was distilled off. To the residue were poured 100 ml of saturated brine, which was extracted with ether(50 ml×3). The organic layer was dried over anhydrous magnesium sulfate, filtered and solvent was distilled off. The residue was purified by means of silica gel column chromatography(hexane:ethyl acetate=10:1) to obtain 1.0 g of (1S,3S,3aS,4aS,8aR,9aS)-1-methoxy-3-methyl-4-methylene-dodecahydronaphtho[2,3-c]furan (yield 86%).

$[\alpha]_D^{20}$+56° (c 0.53, CHCl$_3$); Pale yellow oily product; $^1$H NMR(500 MHZ, CDCl$_3$): δ 0.99–1.33(6H,m) 1.26(3H,d,J=5.8) 1.59–1.73(4H,m) 1.80–1.91(2H,m) 2.25(1H,dt,J=12.2, 6.2) 2.73(1H,dd,J=9.4,6.5) 3.33(3H,s) 4.20(1H,dq,J=9.8, 6.0) 4.58(1H,s) 4.71(1H,s) 4.82(1H,s); $^{13}$C NMR(125 MHZ, CDCl$_3$): δ (21.4, 26.1, 26.4, 28.9, 33.3, 34.5, 41.6, 42.8, 47.9, 53.4, 54.1, 78.2, 109.2, 109.3, 148.8; IR(neat): 2924, 1640, 1451, 1375 cm$^{-1}$; HRCIMS: Calcd. for C$_{15}$H$_{25}$O$_2$: 237.1855 Found: 237.1832;

EXAMPLE 8

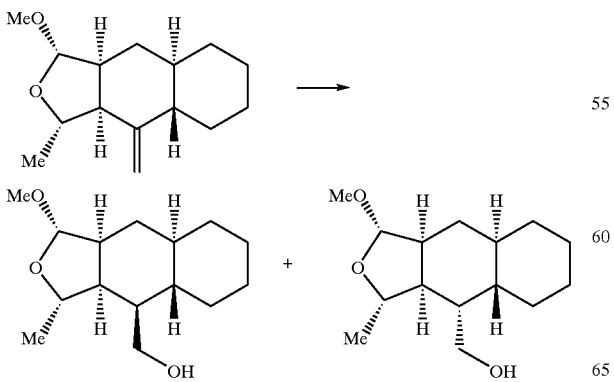

To 99.8 mg(0.42 mmol) of (1S,3S,3aS,4aS,8aR,9aS)-1-methoxy-3-methyl-4-methylene-dodecahydronaphtho[2,3-c]furan in 10 ml of dehydrated tetrahydrofuran solution were added dropwise 633.4 μl (1.5 equivalents) of borane-tetrahydrofuran complex(1M) under cooling with ice and under an atmosphere of argon, and the mixture was stirred for 4.5 hours while raising temperature naturally. The reaction mixture was cooled with ice and 1 ml of water was added to stop the reaction. Then, 0.50 ml of 30% aqueous hydrogen peroxide and 0.50 ml of 10% aqueous solution of sodium hydroxide were added, which was stirred for 30 minutes. Solvent was distilled off and 20 ml of water were poured to the residue, which was extracted with methylene chloride(10 ml×3). The organic layer was dried over anhydrous magnesium sulfate, filtered and solvent was distilled off under reduced pressure. The residue was purified by means of silica gel column chromatography(hexane:ethyl acetate=4:1, then 1:1) to obtain 86.7 mg of (1S,3S,3aR,4R,4aS,8aR,9aS)-4-hydroxymethyl-1-methoxy-3-methyl-dodecahydronaphtho[2,3-c]furan (yield 81%) and 11.7 mg of (1S,3S,3aR,4S,4aS,8aR,9aS)-4-hydroxymethyl-1-methoxy-3-methyl-dodecahydronaphtho[2,3-c]furan (yield 11%). (1S,3S,3aR,4R,4aS,8aR,9aS)-4-hydroxymethyl-1-methoxy-3-methyl-dodecahydronaphtho[2,3-c]furan.

$[\alpha]_D^{20}$+97° (c 0.43, CHCl$_3$); mp. 97–98° C. (hexane) Colorless lattice-like crystals $^1$H NMR(500 MHz, CDCl$_3$): δ 0.84–1.13(6H,m) 1.18–1.29(2H,m) 1.39(3H,d,J=6.0) 1.49–1.81(5H,m) 1.83–1.89(1H,m) 2.17(1H,dt,J=12.4,6.0) 2.40(1H,dt,J=9.1,5.0) 3.33(3H,s) 3.58–3.65(1H,m) 3.74–3.79(1H,m) 4.23(1H,dq,J=9.3,6.0) 4.48(1H,s); $^{13}$C NMR(125 MHz, CDCl$_3$): δ 5 24.2, 26.1, 26.5, 30.2, 33.3, 34.1, 38.7, 40.7, 43.9, 45.2, 46.8, 53.9, 62.9, 75.5, 108.1; IR(KBr): 3453, 2926, 1449, 1395 cm$^{-1}$; Elemental analysis: Calcd. for C$_{15}$H$_{26}$O$_3$; C: 70.83; H: 10.30; Found; C: 70.90; H: 10.49; (1S,3S,3aR,4S,4aS,8aR,9aS)-4-hydroxymethyl-1-methoxy-3-methyl-dodecahydronaphtho[2,3-c]furan.

$[\alpha]_D^{20}$+11° (c 0.46, CHCl$_3$); Colorless oily product; $^1$H NMR(500 MHz, CDCl$_3$): δ 0.82–0.94(2H,m) 1.14–1.33(6H, m) 1.30(3H,d,J=6.0) 1.41–1.81(6H,m) 2.22(1H,dt,J=13.1, 6.3) 2.31(1H,dd,J=9.8,6.3) 3.33(3H,s) 3.56(1H,dd,J=10.6, 8.6) 3.84(1H,dd,J=10.6,4.3) 4.15(1H,dq,J=9.9,6.0) 4.53(1H, s); 13C NMR(125 MHz, CDCl$_3$): δ 21.8, 26.4, 27.2, 30.5, 33.2, 34.9, 35.0, 39.9, 40.0, 42.6, 44.8, 54.1, 63.1, 77.1, 109.3; IR(KBr): 3422, 2922, 1451, 1375 cm$^{-1}$; HRCIMS: Calcd. for C$_{15}$H$_{27}$O$_3$; 255.1960; Found; 255.1942;

REFERENTIAL EXAMPLE 1

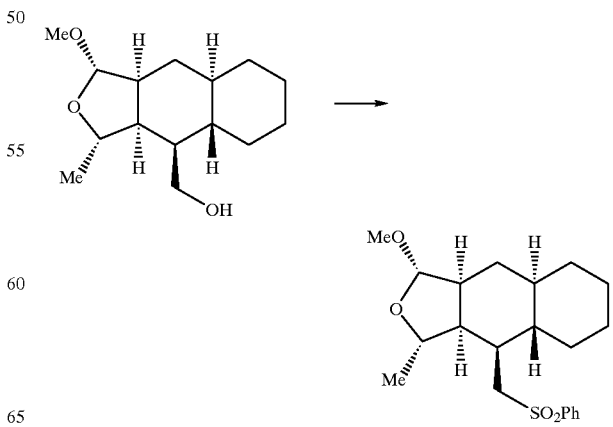

To 460.5 mg(1.81 mmol) of (1S,3S,3aR,4R,4aS,8aR,9aS)-4-hydroxymethyl-1-methoxy-3-methyl-dodecahydronaphtho[2,3-c]furan in 20 ml of ethylene chloride solution were added 20.3 mg(0.1 equivalent) of 4-(dimethylamino)pyridine and 1.26 ml(5 equivalents) of triethylamine, and, after 420.4 μl (3 equivalents) of methanesulfonyl chloride were added dropwise under cooling with ice and under an atmosphere of argon, the mixture was stirred for about 3 hours while raising temperature naturally. To the reaction mixture were added 20 ml of water to wash, and extraction with methylene chloride(3 ml×3) was performed from the aqueous layer. Combined organic layers were dried over anhydrous magnesium sulfate, filtered and solvent was distilled off. The residue was purified by means of silica gel column chromatography(hexane:ethyl acetate= 2:1) to obtain 645.7 mg of O-mesyl form. To 304.7 mg(1.5 equivalents) of potassium t-butoxide in 10 ml of dehydrated dimethyl sulfoxide solution placed in a 25 ml flask were added dropwise 278.8 μl (1.5 equivalents) of thiophenol at room temperature under stirring, and the mixture was stirred for 10 minutes. This was added to previous 645.7 mg of O-mesyl form in 10 ml of dehydrated dimethyl sulfoxide solution, and the mixture was stirred for 3 hours at room temperature. The reaction mixture was poured into 20 ml of cold dilute aqueous solution of sodium hydrogencarbonate, which was extracted with ether(10 ml×3). After washing the organic layer with saturated brine(10 ml×1), it was dried over anhydrous magnesium sulfate, filtered and then solvent was distilled off to obtain phenyl thioether. This was dissolved into 50 ml of methylene chloride and 976.3 mg(2.5 equivalents) of m-chloroperbenzoic acid(80%) and 760.4 mg(5 equivalents) of sodium hydrogencarbonate were added under stirring and cooling with ice. After stirring for 2 hours at room temperature, the reaction mixture was filtered through celite and the residue was washed with methylene chloride(20 ml). Solvent was distilled off under reduced pressure and the residue was diluted with 50 ml of ether, which was washed with saturated aqueous solution of sodium hydrogencarbonate(10 ml×3) and with saturated brine(10 ml×1). The organic layer was dried over anhydrous magnesium sulfate, filtered and solvent was distilled off. The residue was purified by means of silica gel column chromatography(hexane:ethyl acetate=2:1, then 2:1) to obtain 563.9 mg of (1S,3S,3aS,4R,4aS,8aR,9aS)-1-methoxy-3-methyl-4-(phenylsulfonyl)methyl-dodecahydronaphtho[2,3-c]furan (yield after 3 processes 82%).

$[\alpha]_D^{20}$+104° (c 0.35, CHCl$_3$); (Figure in literature·X: $[\alpha]_D^{20}$+100° (c 0.35, CHCl$_3$)) ·X·Kozikowski, A. P. et al, J. Org. Chem., 1997, 62, 5023. mp. 136–137° C. (hexane-ethyl acetate) Colorless powdery crystals; $^1$H NMR(500 MHz, CDCl$_3$): δ 0.63(1H,qd,J=12.2,3.0) 0.85–1.03(4H,m) 1.09–1.24(2H,m) 1.45(3H,d,J=6.1) 1.48–1.77(5H,m) 2.06–2.13(1H,m) 2.19(1H,dt,J=12.4,6.0) 2.77(1H,dt,J=8.8, 5.5) 2.99(1H,dd,J=14.7,9.5) 3.27(1H,dd,J=14.7,1.7) 3.30 (3H,S) 4.09 (1H,dq,J=8.9,6.1) 4.46(1H,s) 7.55–7.61(2H,m) 7.64–7.69(1H,m) 7.89–7.93(2H,m); $^{13}$C NMR(125 MHz, CDCl$_3$): δ 25.7, 25.8, 26.5, 29.9, 33.0, 34.1, 36.7, 40.8, 41.0, 45.0, 46.2, 53.9, 55.7, 75.3, 108.3, 127.9, 127.9, 129.3, 129.3, 133.7, 19.9; IR(KBr): 2917, 1447, 1377, 1319m 1144 cm$^{-1}$; Elemental analysis: Calcd. for C$_{21}$H$_{30}$O$_4$S; C: 66.63; H: 7.99; Found; C: 66.33; H: 8.15.

REFERENTIAL EXAMPLE 2

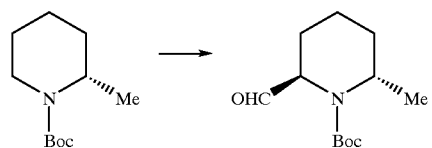

To 2.50 g(12.5 mmol) of (S)-N-tert-butoxycarbonyl-2-methylpiperidine in 25 ml of dehydrated diethyl ether solution were added 1.89 ml(1 equivalent) of N,N,N',N'-tetramethylethylenediamine at –60° C. under an atmosphere of argon, and then 13.3 ml(1.1 equivalent) of sec-butyllithium were added dropwise. After the temperature of reaction mixture was raised to –20° C., it was cooled again to –70° C. and 1.46 ml(1.5 equivalents) of N,N-dimethylformamide were added dropwise. After stirring for about 2 hours, 20 ml of saturated solution of ammonium chloride were added to the reaction mixture to stop the reaction. The aqueous layer was separated, which was extracted with ether(10 ml×3). Combined organic layers were dried over anhydrous magnesium sulfate, filtered and solvent was distilled off. The residue was purified by means of silica gel column chromatography(hexane:ethyl acetate= 8:1) to obtain 1.58 g of (2R,6S)-tert-butyl 2-formyl-6-methyl-1-piperidinecarboxylate (yield 55%).

$[\alpha]_D^{26}$+120° (c 1.03, CHCl$_3$); (Figure in literature·X: $[\alpha]_D^{20}$+122° (c 0.96, CHCl$_3$)) ·X·Kozikowski, A. P. et al, J. Org. Chem., 1997, 62, 5023. $^1$H NMR(400 MHz, CDCl$_3$): δ 1.12(3H,d,J=6.9) 1.46(9H,s) 1.36–1.77(6H,m) 3.63(1H,dt, J=11.3,3.9) 4.27(1H,brs) 9.30(1H,d,J=3.4).

REFERENTIAL EXAMPLE 3

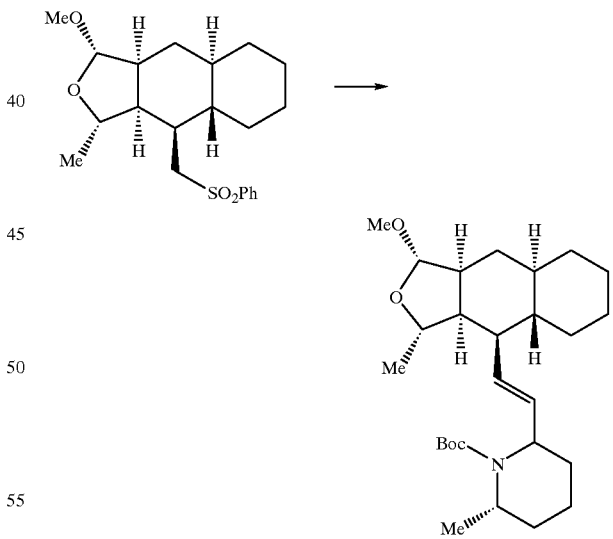

To 201.0 mg(0.53 mmol) of (1S,3S,3aS,4R,4aS,8aR,9aS)-1-methoxy-3-methyl-4-(phenylsulfonyl)methyl-dodecahydronaphtho[2,3-c]furan in 10 ml of dehydrated dimethoxyethane solution were added dropwise 689.6 μl(2 equivalents) of n-butyllithium-hexane solution(1.54M) at –78° C. (external temperature) under an atmosphere of argon. After stirring for 10 minutes, 241.4 mg(2 equivalents) of (2R,6S)-tert-butyl 2-formyl-6-methyl-1-piperidinecarboxylate in 2 ml of dehydrated dimethoxyethane solution were added dropwise, which was stirred for 1 hour while raising temperature naturally. To the reaction mixture were added 10 ml of water to stop the reaction, which was diluted with 20 ml of saturated brine and extracted with ether(10 ml×3). The organic layer was dried over anhydrous magnesium sulfate, filtered and solvent was distilled off. The residue was purified by means of silica gel column chromatography(hexane:ethyl acetate=9:1, then 1:1) to obtain 145.0 mg(yield 45%) of coupling resultant as a mixture of diastereomer together with 111.0 mg(yield 55%) of starting material (1S,3S.,3aS,4R,4aS,8aR,9aS)-1-methoxy-3-methyl-4-(phenylsulfonyl)methyl-dodecahydronaphtho[2,3-c]furan. The $^1$H NMR(400 MHz, CDCl$_3$) spectrum of this compound showed signals of complicated mixture, but, since four signals of δ 1.46(9H,s), δ 3.34(3H,s),δ 7.90–8.04(3H,m) and δ 7.52–7.68(2H,m) could be identified, the inventors assumed this as a coupling resultant.

To 333.9 mg of said coupling resultant in 14 ml of methanol solution were added 5.96 g of sodium amalgam (5%) and 1.08 g of disodium hydrogenphosphate at room temperature under stirring, and the mixture was stirred for 2.5 hours. To the reaction mixture were added 10 ml of water to stop the reaction and solvent was distilled off under reduced pressure. The residue was diluted with 20 ml of saturated brine, which was extracted with ether(10 ml×3). The organic layer was dried over anhydrous magnesium sulfate, filtered and solvent was distilled off. The residue was purified by means of silica gel column chromatography (hexane:ethyl acetate=5:1) to obtain 162.4 mg of (2R,6S)-tert-butyl 2-[(E)-2-[(1S,3S,3aR,4R,4aS,8aR,9aS)-1-methoxy-3-methyl-dodecahydronaphtho[2,3-c]furan-4-yl]vinyl]- 6-methyl-1-piperidinecarboxylate(yield after 2 processes 66%).

$[\alpha]_D^{25}$+102° (c 0.43, CHCl$_3$); (Figure in literature·X: $[\alpha]_D^{20}$+90.5° (c 0.38, CHCl$_3$) ·X·Kozikowski, A. P. et al, J. Org. Chem., 1997, 62, 5023. mp. 90.5–92.5° C. Colorless powdery crystals $^1$H NMR(400 MHZ, CDCl$_3$): δ 0.63–0.74 (1H,m) 0.87–1.01(4H,m) 1.16–1.34(3H,m) 1.23(3H,d,J= 6.9) 1.29(3H,d,J=5.9) 1.44(9H,s) 1.46–1.79(8H,m) 1.87–2.08(3H,m) 2.14–2.22(2H,m) 3.31(3H,s) 3.95–4.02 (1H,m) 4.18(1H,dq,J=8.3,6.4) 4.41(1H,brs) 4.48(1H,s) 5.21 (1H,dd,J=15.2,10.3) 5.47(1H,dd,J=15.2,6.4); HREIMS: Calcd. for C$_{27}$H$_{45}$NO$_4$; 447.3349 Found; 447.3342.

REFERENTIAL EXAMPLE 4

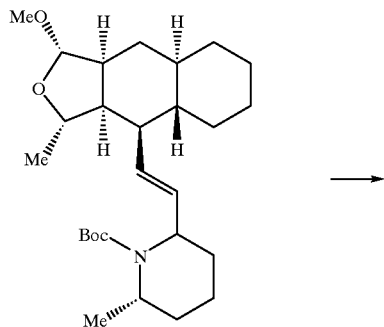

⟶

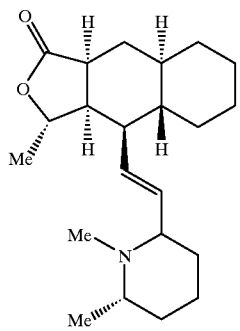

To 154.7 mg(0.35 mmol) of (2R,6S)-tert-butyl-2-[(E)-2-[(1S,3S,3aR,4R,4aS,8aR,9aS)-1-methoxy-3-methyl-dodecahydronaphtho[2,3-c]furan-4-yl]vinyl]-6-methyl-1-piperidinecarboxylate in 6 ml of acetone solution were added 0.90 ml of Jones reagent at room temperature under stirring. After stirring for 30 minutes, 10 ml of water were added to the reaction mixture to stop the reaction and solvent was distilled off under reduced pressure. The residue was diluted with 10 ml of saturated brine, which was extracted with ether(5 ml×3). The organic layer was dried over anhydrous magnesium sulfate, filtered and solvent was distilled off to obtain crude (2R,6S)-tert-butyl 2-[(E)-2-[(3S,3aR,4R, raS,8aR,9aS-3-methyl-1-oxo-dodecahydronaphtho[2,3-c]furan-4-yl)vinyl]-6-methyl-1-piperidinecarboxylate. To this were added 2 ml of methylene chloride to make a solution, and 1.00 ml of trifluoroacetic acid was added, which was stirred for 1.5 hours at room temperature. To the reaction mixture were added 20 ml of cold dilute aqueous solution of sodium hydroxide to make alkaline, and solvent was distilled off under reduced pressure. The residue was extracted with ether(5 ml×3). The organic layer was dried over anhydrous magnesium sulfate, filtered and solvent was distilled off to obtain 133.2 mg of crude (3s,3aR,4R,ras,8aR,9as)-3-methyl-4-[(E)-2-[(2R,6S)-6-methylpiperidin-2-yl]vinyl-3-methyl-decahydronaphtho[2,3-c]furan-1(3H)-one.

To 133.2 mg of crude (3S,3aR.4R,4aS,8aR,9aS)-3-methyl-4-[(E)-2-[(2R,6S)-6-methylpiperidine-2-yl]vinyl)-3-methyl-decahydronaphtho[2,3-c]furan-1(3H)-one in 6 ml of acetonitrile solution were added 0.30 ml of 37% formaldehyde solution and then 47.8 mg(2.2 equivalents) of sodium cyanoborohydride at room temperature under stirring, and the mixture was stirred for 30 minutes. Acetic acid was added to the reaction mixture to make neutral and, after stirring further for 1 hour, 20 ml of cold dilute aqueous solution of sodium hydroxide were added to make alkaline and solvent was distilled off under reduced pressure. The residue was extracted with ether(10 ml×3). The organic layer was dried over anhydrous magnesium sulfate, filtered and solvent was distilled off. the residue was purified by means of silica gel column chromatography(hexane:ethyl acetate=5:1, then 1:1) to obtain 108.8 mg of (3S,3aR,4R, 4aS,8aR,9aS)-4-[(E)-2-[(2R,6S)-1.6-dimethylpiperidine-2-yl]vinyl)-3-methyl-decahydronaphtho[2,3-c]furan-1(3H)-one(himbacine)(yield after 3 processes 91%).

$[\alpha]_D^{24}$+550 (c 0.21, CHCl$_3$); Standard article·X· $[\alpha]_D^{24}$+ 56 (c 0.21, CHCl$_3$); ·X·Sample purchased from Sigma Corp. (Figure in literature·X:

$[\alpha]_D^{20}$+51.4" (c 1.01, CHCl$_3$)·X·Kozikowski, A. P. et al, J. Org. Chem., 1997, 62, 5023.); mp. 127–128° C. (hexane) Colorless powdery crystals Standard article·X· mp. 128–129° C. (hexane) Colorless powdery crystals;

*Sample purchased from Sigma Corp. (Figure in literatures*: mp. 129–130° C.; *Kozikowski, A. P. et al, J. org. Chem., 1997, 62, 5023); $^1$H NMR(400 MHz, CDCl$_3$): δ 0.70–0.75(1H,m) 0.93–1.06(3H,m) 1.00(3H,d,J=6.4) 1.12–1.28(3H,m) 1.38–1.47(2H,m) 1.40(3H,d,J=6.4) 1.50–1.61(2H,m) 1.64–1.80(6H,m) 1.87(1H,ddd,J=13.2,5.9, 2.4) 2.07–2.14(1H,m) 2.22(3H,s) 2.22–2.27(1H,m) 2.63 (1H,dt,J=13.2,6.7) 2.80–2.87(1H,m) 2.99–3.06(1H,m) 4.63 (1H,dq,J=11.0,5.9) 5.26(1H,dd,J=15.2,9.8) 5.58)1H,dd,J= 15.0,9.1); $^{13}$C NMR(100 MHz, CDCl$_3$): δ 14.0, 19.0, 22.2, 26.1, 26.5, 31.5, 32.1, 32.6, 33.3, 33.6, 39.9, 41.2, 41.6, 42.3, 45.8, 49.2, 53.4, 61.4, 76.8, 133.4, 133.6, 178.3; IR(KBr): 2932, 2848, 1793, 1449 cm$^{-1}$; HREIMS: Calcd. for C$_{22}$H$_{35}$NO$_2$; 345.2688; Found; 345.2696.

EXAMPLE 9

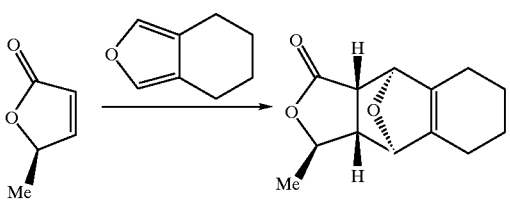

Similarly to Example 1, 1.37 g(13.9 mmol) of (R)-5-methyl-2(5H)-furanone and 1.70 g(1 equivalent) of 4,4,6,7-tetrahydroisobenzofuran in 2 ml of dehydrated ether solution were reacted with 1.06 g of lithium perchlorate to obtain 2.20 g of (3R,3aR,4R,9S,9aS)-4,9-epoxy-3-methyl-3a,4,5,6,7,8,9,9a-octahydronaphtho[2,3-c]furan-1(3H)-one(yield 72%).

EXAMPLE 10

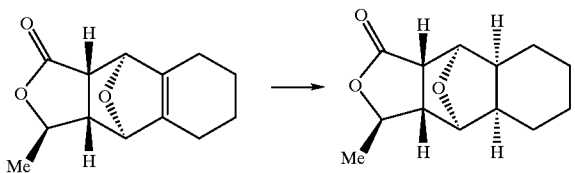

Similarly to Example 2, 0.22 g(10% by weight) of 10% palladium-carbon were added to 2.20 g(9.99 mmol) of (3R,3aR,4R,9S,9aS)-4,9-epoxy-3-methyl-3a,4,5,6,7,8,9,9a-octahydronaphtho[2,3-c]furan-1(3H)-one in 5 ml of ethanol solution and catalytic reduction was conducted at ambient temperature under 98.1 Kpa to obtain 1.36 g of (3R,3aR, 4S,4aR,8aS,9R,9aS)-4,9-epoxy-3-methyl-decahydronaphtho[2,3-c]furan-1(3H)-one(yield 61%).

$[α]_D^{23}$–50° (c 0.68, CHCl$_3$); mp.148–149° C. (hexane-ethyl acetate) Colorless flaky crystals.

EXAMPLE 11

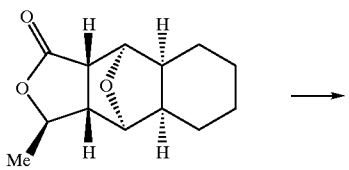

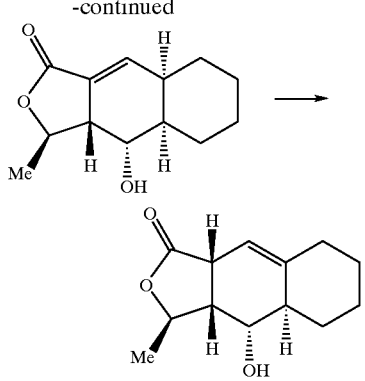

Similarly to Example 3, 1.35 g(6.07 mmol) of (3R,3aR, 4S,4aR,8aS,9R,9aS)-4,9-epoxy-3-methyl-decahydronaphtho[2,3-c]furan-1(3H)-one were reacted with 27.6 mg(5 equivalents) of lithium bis(trimethylsilyl)amide-tetrahydrofuran solution(1.1M) to obtain 1.37 g of (3R,3aR, 4S,4aR,8aS)-4-hydroxy-3-methyl-3a,4,4a,5,6,7,8,8a-octahydronaphtho[2,3-c]furan-1(3H)-one and then reacted with 4.54 ml(5 equivalents) of 1,8-diazabicyclo[5.4.0] undec-7-ene to obtain 1.05 g of (3R,3aR,4S,4aR,9aR)-4-hydroxy-3-methyl-3a,4,4a,5,6,7,8,9a-octahydronaphtho[2, 3-c]furan-1(3H)-one(yield after 2 processes 78%).

$[α]_D^{16}$–160° (c 0.27, CHCl$_3$); mp.156–157° C. (hexane-ethyl acetate) Colorless lattice-like crystals.

EXAMPLE 12

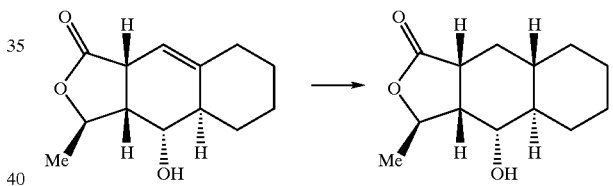

Similarly to Example 4, 1.04 g(4.68 mmol) of (3R,3aR, 4S,4aR,9aR)-4-hydroxy-3-methyl-3a,4,4a,5,6,7,8,9a-octahydronaphtho[2,3-c]furan-1(3H)-one were catalytically reduced at ambient temperature under 98.1 KPa of (3R,3aR, 4S,4aR,8aS,9aR)-4-hydroxy-3-methyl-decahydronaphtho [2,3-c]furan-1(3H)-one(yield 93%).

$[α]_D^{22}$+69° (c 0.33, CHCl$_3$); mp. 185–186° C. (hexane-ethyl acetate) Colorless platy crystals.

EXAMPLE 13

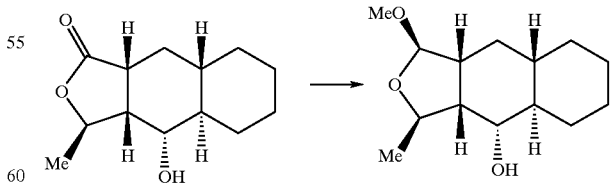

Similarly to Example 5, 0.98 g(4.37 mmol) of (3R,3aR, 4S,4aR,8aS,9aR)-4-hydroxy-3-methyl-decahydronaphtho [2,3-c]furan-1(3H)-one were reacted with 13.8 ml(3 equivalents) of diisobutylaluminum hydride-hexane solution(0.95M) to convert to crude lactol form and then reacted with 20 ml of methanol and 0.81 ml(1.5 equivalents) of boron trifluoride-diethyl ether complex to obtain 0.89 g of (1R,3R,3aR,4S,4aR,8aS,9aR)-4-hydroxy-1-methoxy-3-methyl-decahydronaphtho[2,3-c]furan(yield after 2 processes 85%).

$[\alpha]_D^{21}$+95° (c 0.34, CHCl$_3$); mp. 118–119° C. (hexane) Colorless needle-like crystals.

EXAMPLE 14

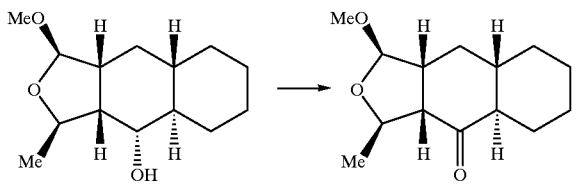

Similarly to Example 6, 866.0 g(3.60 mmol) of (1R,3R,3aR,4S,4aR,8aS,9aR)-4-hydroxy-1-methoxy-3-methyl-decahydronaphtho[2,3-c]furan were oxidized with 63.3 mg(0.05 equivalents) of tetrapropylammonium perruthenate, 633.2 mg(1.5 equivalents) of N-methylmorpholine and 1.80 g of MS4A to obtain 786.0 mg of (1R,3R,3aS,4aR,8aS,8aS,9aR)-1-methoxy-3-methyl-4-oxo-dodecahydronaphtho[2,3-c]furan(yield 92%).

$[\alpha]_D^{21}$+165° (c 0.41, CHCl$_3$); mp. 86–87° C. (hexane) Colorless platy crystals.

EXAMPLE 15

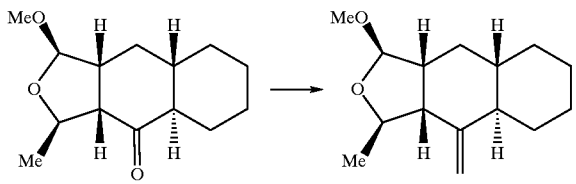

Similarly to Example 7, 6665.6 mg(5 equivalents) of methyltriphenylphosphonium iodide and 16.5 ml(5 equivalents) of sodium bis(trimethylsilyl)amide-toluene solution(1M) were reacted with 786.0 mg of (1R,3R,3aS,4aR,8aS,9aR)-1-methoxy-3-methyl-4-oxo-dodecahydronaphtho[2,3-c]furan to obtain 683.5 mg of (1R,3R,3aR,4aR,8aS,9aR)-1-methoxy-3-methyl-4-methylene-dodecahydronaphtho[2,3-c]furan(yield 88%).

$[\alpha]_D^{23}$+58° (c 0.29, CHCl$_3$); Pale yellow oily product.

EXAMPLE 16

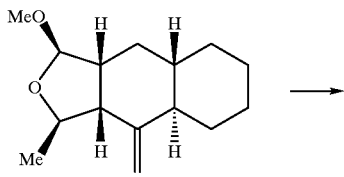

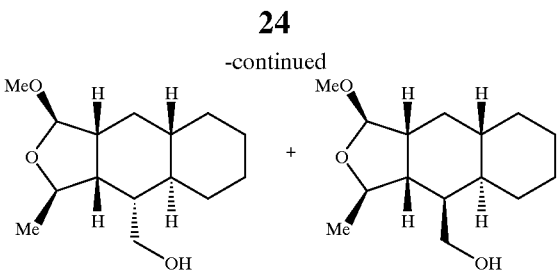

Similarly to Example 8, after 663.7 mg(2.81 mmol) of (1R,3R,3aR,4aR,8aS,9aR)-1-methoxy-3-methyl-4-methylene-dodecahydronaphtho[2,3-c]furan were reacted with 4.21 ml (1.5 equivalents) of borane-tetrahydrofuran complex(1M), it was oxidized by adding 3.00 ml of 30% hydrogen peroxide solution and 3.00 ml of 10% aqueous solution of sodium hydroxide to obtain 538.2 mg of (1R,3R,3aS,4S,4aR,8aS,9aR)-4-hydroxymethyl-1-methoxy-3-methyl-dodecahydronaphtho[2,3-c]furan(yield 75%) and 55.2 mg of (1R,3R,3aS,4R,4aR,8aS,9aR)-4-hydroxymethyl-1-methoxy-3-methyl-dodecahydronaphtho[2,3-c]furan (8%). (1R,3R,3aS,4S,4aR,8aS,9aR)-4-hydoxymethyl-1-methoxy-3-methyl-dodecahydronaphtho[2,3-c]furan $[\alpha]_D^{22}$+84° (c 0.53, CHCl$_3$); mp. 93–94° C. (hexane) Colorless needle-like crystals; (1R,3R,3aS,4R,4aR,8aS,9aR)-4-hydroxymethyl-1-methoxy-3-methyl-dodecahydronaphtho[2,3-c]furan; $[\alpha]_D^{22}$+10° (c 0.42, CHCl$_3$); Yellow oily product.

REFERENTIAL EXAMPLE 5

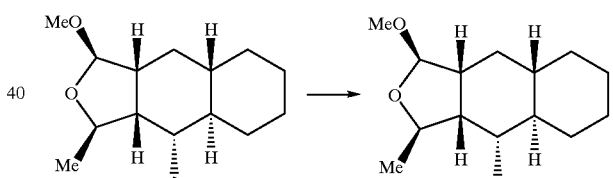

similarly to Referential example 1, 532.4 mg(2.09 mmol) of (1R,3R,3aS,4S,4aR,8aS,9aR)-4-hydroxymethyl-1-methoxy-3-methyl-dodecahydronaphtho[2,3-c]furan were mesylated with 486.0 μl(3 equivalents) of methanesulfonyl chloride, 1458.6 μl (5 equivalents) of triethylamine and 23.5 mg(0.1 equivalent) of 4-(dimethylamino)pyridine to obtain 687.5 mg of yellow oily O-mesyl form. Then, this was converted to phenylthio form with 348.1 mg(1.5 equivalents) of potassium t-butoxide and 318,5 μl (1.5 equivalents) of thiophenol and further oxidized with 1290.0 mg(2.5 equivalents) of m-chloroperbenzoic acid(70%) and 879.2 mg(5 equivalents) of sodium hydrogencarbonate to obtain 311.2 mg of (1R,3R,3aR,4S,4aR,8aS,9aR)-1-methoxy-3-methyl-4-(phenylsulfonyl)methyl-dodecahydronaphtho[2,3-c]furan(yield after 3 processes 39%).

$[\alpha]_D^{22}$−104° (c 0.35, CHCl$_3$); mp. 129–130° C. (hexane-ethyl acetate) Colorless powdery crystals.

REFERENTIAL EXAMPLE 6

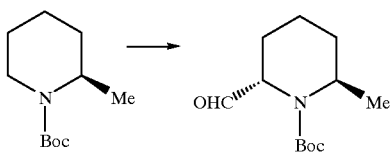

Similarly to Referential example 2, 2.10 g(10.5 mmol) of (R)-N-tert-butoxycarbonyl-2-methylpiperidine were reacted with 1.59 ml(1 equivalent) of N,N,N',N'-tetramethylethylenediamine, 111.1 ml (1.1 equivalent) of sec-butyllithium(1.04M) and 1.22 ml(1.5 equivalents) of N,N-dimethylformamide to obtain 1.67 g of (2S,6R)-tert-butyl 2-formyl-6-methyl-1-piperidinecarboxylate(yield 70%).

$[\alpha]_D^{22}$+128° (c 0.82, CHCl$_3$);

REFERENTIAL EXAMPLE 7

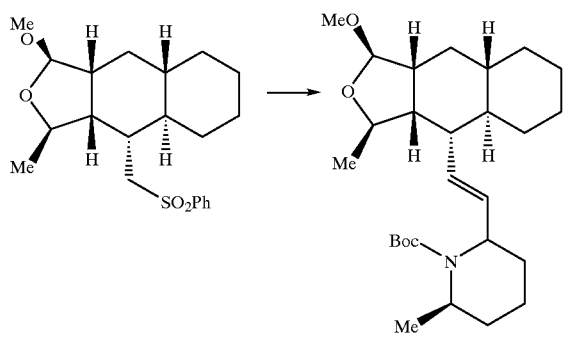

Similarly to Referential example 3, 282.9 mg(0.75 mmol) of (1R,3R,3aR,4S,4aR,8aS,9aR)-1-methoxy-3-methyl-4-(phenylsulfonyl)methyl-dodecahydronaphtho[2,3-c]furan were reacted with 952.1 μl (2 equivalents) of n-butyllithium-hexane solution(1.57M) and then with 339.8 mg(2 equivalents) of (2S,6R)-tert-butyl 2-formyl-6-methyl-1-piperidinecarboxylate to obtain 233.7 mg(yield 52%) of coupling resultant as a mixture of diastereomer together with 135.7 mg(48%) of starting material (1R,3R,3aR,4S,4aR,8aS,9aR)-1-methoxy-3-methyl-4-(phenylsulfonyl)methyl-dodecahydronaphtho[2,3-c]furan. Then, 5.50 g of sodium amalgam(5%) and 1.00 g of disodium hydrogenphosphate were reacted to obtain 110.2 mg of (2S,6R)-tert-butyl 2-[(E)-2-(1R,3R,3aS,4S,4aR,8aS,9aR)-1-methoxy-3-methyl-dodecahydronaphtho[2,3-c]furan-4-yl]vinyl]-6-methyl-1-piperidinecarboxylate(yield after 2 processes 64%).

$[\alpha]_D^{23}$+88° (c 0.35, CHCl$_3$); mp. 90–92° C. Colorless powdery crystals.

REFERENTIAL EXAMPLE 8

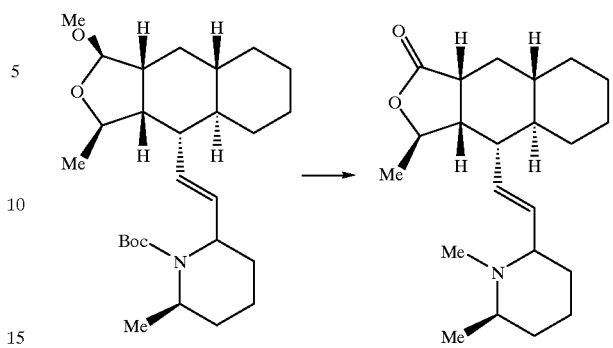

Similarly to Referential example 4, 156.0 mg(0.35 mmol) of (2S,6R)-tert-butyl 2-[(E)-2-[(1R,3R,3aS,4S,4aR,8aS,9aR)-1-methoxy-3-methyl-dodecahydronaphtho[2,3-c]furan-4-yl]vinyl]-6-methyl-1-piperidinecarboxylate were reacted with 0.90 ml of Jones reagent to obtain 147.1 mg of (2S,6R)-tert-butyl 2-[(E)- 2-[(3R,3aS,4S,4aR,8aS,9aR)-3-methyl-1-oxo-dodecahydronaphtho[2,3-c]furan-4-yl]vinyl]-6-methyl-1-piperidinecarboxylate, and then 1.00 ml of trifluoroacetic acid was reacted to obtain 113.0 mg of crude (3R,3aS,4S,4aR,8aS,9aR)-3-methyl-4-[(E)-2-[(2S,6R)-6-methylpiperidine-2-yl]vinyl]-3-methyl-decahydronaphtho [2,3-c]furan-1(3H)-one(yield after 2 processes 98%). Then, 0.30 ml of 37% formaldehyde solution and 47.1 mg (2.2 equivalents) of sodium cyanoboronhydride were reacted to obtain 100.8 mg of (3R,3aS,4S,4aR,8aS,9aR)-4-[(E)-2-[(2S,6R)-1.6-dimethylpiperidine-2-yl]vinyl]-3-methyl-decahydronaphtho[2,3-c]furan-1(3H)-one (ent-himbacine) (yield after 3 processes 84%).

$[\alpha]_D^{23}$+59° (c 0.29, CHCl$_3$); mp. 128–130° C. (hexane) Colorless powdery crystals.

What is claimed is:

1. A hydronaphtho[2,3-c]furan compound represented by formula (1)

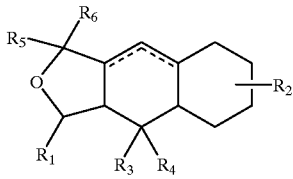

(1)

wherein $R_1$ denotes a lower alkyl group or substituted or unsubstituted aralkyl group, $R_2$ denotes a hydrogen atom, lower alkyl group or substituted or unsubstituted aralkyl group, $R_3$ and $R_4$ together denote an oxygen atom or methylene group, or $R_3$ denotes a hydrogen atom and $R_4$ denotes a hydroxyl group, lower alkoxy group, substituted or unsubstituted aralkyloxy group or lower acyloxy group, $R_5$ and $R_6$ together denote an oxygen atom, or $R_5$ denotes a hydrogen atom and $R_6$ denotes a hydroxyl group, lower alkoxy group, substituted or unsubstituted aralkyloxy group or lower acyloxy group, and, in the case of broken line accompanied, one denotes single bond and the other denotes double bond, or both denote single bonds.

2. A hydronaphtho[2,3-c]furan compound represented by formula (1-1)

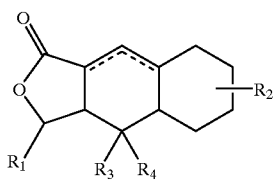

(1-1)

wherein $R_1$ denotes a lower alkyl group or substituted or unsubstituted aralkyl group, $R_2$ denotes a hydrogen atom, lower alkyl group or substituted or unsubstituted aralkyl group, $R_3$ and $R_4$ together denote an oxygen atom or methylene group, or $R_3$ denotes a hydrogen atom and $R_4$ denotes a hydroxyl group, lower alkoxy group, substituted or unsubstituted aralkyloxy group or lower acyloxy group, and, in the case of broken lines accompanied, one denotes a single bond and the other denotes a double bond, or both denote single bonds.

3. A hydronaphtho[2,3-c]furan compound represented by formula (1-2)

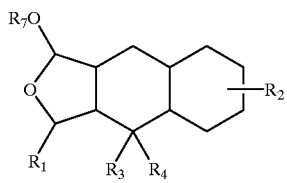

(1-2)

wherein $R_1$ denotes a lower alkyl group or substituted or unsubstituted aralkyl group, $R_2$ denotes a hydrogen atom, lower alkyl group or substituted or unsubstituted aralkyl group, $R_3$ and $R_4$ together denote an oxygen atom or methylene group, or $R_3$ denotes a hydrogen atom and $R_4$ denotes a hydroxyl group, lower alkoxy group, substituted or unsubstituted aralkyloxy group or lower acyloxy group, and $R_7$ denotes a hydrogen atom, lower alkyl group, substituted or unsubstituted aralkyl group or lower acyl group.

4. A hydronaphtho[2,3-c]furan compound represented by formula (2)

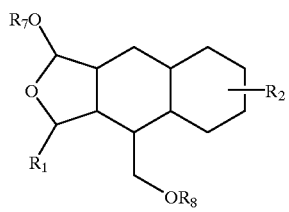

(2)

wherein $R_1$ denotes a lower alkyl group or substituted or unsubstituted aralkyl group, $R_2$ denotes a hydrogen atom, lower alkyl group or substituted or unsubstituted aralkyl group, $R_7$ denotes a hydrogen atom, lower alkyl group, substituted or unsubstituted aralkyl group or lower acyl group, and $R_8$ denotes a hydrogen atom or protective group of hydroxyl group.

5. A hydronaphtho[2,3-c]furan compound represented by formula (3)

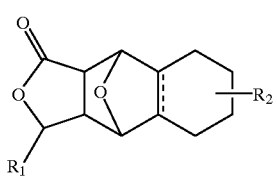

(3)

wherein $R_1$ denotes a lower alkyl group or substituted or unsubstituted aralkyl group, $R_2$ denotes a hydrogen atom, lower alkyl group or substituted or unsubstituted aralkyl group, and, in the case of broken line accompanied, it denotes single bond or double bond.

6. A process for preparing a compound represented by formula (3a)

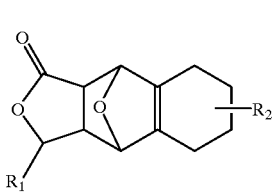

(3a)

wherein $R_1$ denotes a lower alkyl group or substituted or unsubstituted aralkyl group, and $R_2$ denotes a hydrogen atom, lower alkyl group or substituted or unsubstituted aralkyl group, comprising:

reacting a compound represented by formula (4)

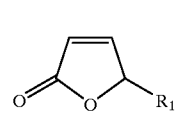

(4)

wherein $R_1$ denotes a lower alkyl group or substituted or unsubstituted aralkyl group, with a compound represented by formula (5)

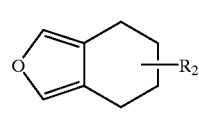

(5)

wherein $R_2$ denotes a hydrogen atom, lower alkyl group or substituted or unsubstituted aralkyl group.

* * * * *

UNITED STATES PATENT AND TRADEMARK OFFICE
CERTIFICATE OF CORRECTION

PATENT NO.   : 6,392,059 B1
DATED        : May 21, 2002
INVENTOR(S)  : Terashima et al.

It is certified that error appears in the above-identified patent and that said Letters Patent is hereby corrected as shown below:

<u>Title page,</u>
Item [73], should read
-- [73]           Assignee:           Sagami Chemical Research Center, Sagamihara-shi; Kyorin Pharmaceutical Co., Ltd., Tokyo, both of (JP) --

Signed and Sealed this

Fourteenth Day of January, 2003

JAMES E. ROGAN
*Director of the United States Patent and Trademark Office*